(12) United States Patent
Choi et al.

(10) Patent No.: US 12,109,557 B2
(45) Date of Patent: Oct. 8, 2024

(54) CATALYST MODULE FOR REMOVING HARMFUL GAS AND MANUFACTURING METHOD THEREFOR, CATALYST SYSTEM COMPRISING SAME FOR REMOVING HARMFUL GAS, HARMFUL SUBSTANCE REMOVING APPARATUS COMPRISING CATALYST MODULE FOR REMOVING RESIDUAL OZONE AND MANUFACTURING METHOD THEREFOR, AND HARMFUL SUBSTANCE REMOVING SYSTEM COMPRISING SAME

(71) Applicant: KOREA INSTITUTE OF MATERIALS SCIENCE, Gyeongsangnam-do (KR)

(72) Inventors: Joon Hwan Choi, Gyeongsangnam-do (KR); Giyeong Kim, Gyeongsangnam-do (KR)

(73) Assignee: KOREA INSTITUTE OF MATERIALS SCIENCE, Changwon-si (KR)

( * ) Notice: Subject to any disclaimer, the term of this patent is extended or adjusted under 35 U.S.C. 154(b) by 0 days.

(21) Appl. No.: 18/007,064

(22) PCT Filed: Oct. 19, 2020

(86) PCT No.: PCT/KR2020/014274
§ 371 (c)(1),
(2) Date: Jan. 27, 2023

(87) PCT Pub. No.: WO2022/030682
PCT Pub. Date: Feb. 10, 2022

(65) Prior Publication Data
US 2023/0271173 A1     Aug. 31, 2023

(30) Foreign Application Priority Data

Aug. 7, 2020   (KR) .................. 10-2020-0099317
Aug. 7, 2020   (KR) .................. 10-2020-0099318

(51) Int. Cl.
| | | |
|---|---|---|
| B01J 35/00 | (2024.01) | |
| B01J 21/04 | (2006.01) | |
| B01J 23/44 | (2006.01) | |
| B01J 35/10 | (2006.01) | |
| B01J 35/33 | (2024.01) | |
| B01J 35/60 | (2024.01) | |
| B01J 37/02 | (2006.01) | |

(52) U.S. Cl.
CPC .............. B01J 35/19 (2024.01); B01J 21/04 (2013.01); B01J 23/44 (2013.01); B01J 35/33 (2024.01); B01J 35/60 (2024.01); B01J 37/0228 (2013.01)

(58) Field of Classification Search
CPC .... B01J 35/0006; B01J 35/0033; B01J 35/10; B01J 21/04; B01J 23/44; B01J 37/0228
See application file for complete search history.

(56) References Cited

U.S. PATENT DOCUMENTS

| | | | |
|---|---|---|---|
| 9,200,552 B2 | 12/2015 | Hirai et al. | |
| 10,183,252 B2 * | 1/2019 | Robinson | B01J 35/1019 |
| 2017/0333842 A1 | 11/2017 | Robinson et al. | |
| 2020/0055039 A1 * | 2/2020 | Kayada | F01N 3/035 |

FOREIGN PATENT DOCUMENTS

| | | | |
|---|---|---|---|
| JP | 09159198 A * | 6/1997 | |
| JP | 5206730 B2 | 6/2013 | |
| JP | 2013-158678 A | 8/2013 | |
| KR | 2017-0078725 A | 7/2017 | |
| KR | 2018-0104207 A | 9/2018 | |
| KR | 2019-0001736 A | 1/2019 | |
| KR | 2019-0000735 | 3/2019 | |
| KR | 2019-0132101 A | 11/2019 | |
| WO | 2018-159214 A1 | 9/2018 | |

OTHER PUBLICATIONS

Pelissier et al., Ceramics International, (1998), v.24, p. 371-377.*
International Search Report for corresponding International Application No. PCT/KR2020/014274 mailed May 4, 2021.
Written Opinion for corresponding International Application No. PCT/KR2020/014274 dated May 4, 2021.
Office Action dated Feb. 21, 2022 for corresponding Korean Application No. 10-2020-0099317 and English translation.
Final Office Action dated Sep. 27, 2022 for corresponding Korean Application No. 10-2020-0099317 and English translation.
Notice of Allowance dated Oct. 6, 2022 for corresponding Korean Application No. 10-2020-0099317 and English translation.

* cited by examiner

*Primary Examiner* — Yong L Chu
(74) *Attorney, Agent, or Firm* — Pearne & Gordon LLP

(57) ABSTRACT

The present invention provides a catalyst module for removing harmful gas, wherein an oxidation reaction or reduction reaction of harmful gas is carried out in a self-heating heating carrier. According to an embodiment of the present invention, the catalyst module for removing harmful gas comprises: a heating carrier composed of an electrically heatable heating body, including one or more flow channels inside, and having a porous structure with pores; and a catalyst region formed on at least a portion of the surface of the heating carrier including the flow channels and containing a catalyst material for promoting a decomposition reaction of harmful gas passing through the flow channels, wherein the catalyst region comprises: a first catalyst layer having a first catalyst material loading amount in the pores of the heating carrier; and a second catalyst layer applied on the inner surface of the heating carrier.

13 Claims, 11 Drawing Sheets

CATALYST MODULE FOR REMOVING HARMFUL GAS AND MANUFACTURING METHOD THEREFOR, CATALYST SYSTEM COMPRISING SAME FOR REMOVING HARMFUL GAS, HARMFUL SUBSTANCE REMOVING APPARATUS COMPRISING CATALYST MODULE FOR REMOVING RESIDUAL OZONE AND MANUFACTURING METHOD THEREFOR, AND HARMFUL SUBSTANCE REMOVING SYSTEM COMPRISING SAME

TECHNICAL FIELD

The present invention relates to a catalyst module for removing harmful gas harmful to the human body, and more specifically, a catalyst module for removing harmful gas, wherein an oxidation reaction or reduction reaction of harmful gas is carried out in a self-heating heating carrier, a manufacturing method therefor, a catalyst system comprising the same for removing harmful gas, a harmful substance removing apparatus comprising a catalyst module for removing residual ozone that removes ozone remaining after being used for removing harmful substances, a manufacturing method therefor, and a harmful substance removing system comprising the same.

BACKGROUND ART

Recently, as interest in the environment increases, a great attention has been paid to technologies for protecting living environments from hazardous environments. In particular, technologies for effectively removing harmful gases that are toxic to the human body or greatly change the atmospheric environment have been actively researched in recent years. These harmful gases include various substances and organisms that are used in chemical processes and are fatally toxic to the human body. For example, among the harmful gases, volatile organic compounds contain many first-class carcinogens designated by the World Health Organization (WHO). Exposure for a long time to such harmful gases may cause reduced immunity thereby contributing to development of a variety of serious diseases including respiratory diseases such as colds, asthma, bronchitis, etc., cardiovascular diseases, skin diseases, eye diseases, and the like. In addition, as the representative precursor substances of fine particles, the harmful gases may form secondary fine particles in the atmospheric air when they are discharged, threating the human health and deteriorating the air quality.

Technologies for removing harmful gases through chemical decomposition use catalysts to accelerate the decomposition reaction. In a reaction using a catalyst, the catalyst is heated to a normal operating temperature range and used in order to maximize the catalyst efficiency. In general, a heating source is disposed outside the catalyst module, and when external heating is used, energy loss is large, and hence the external heating is not suitable for fields requiring low energy. In addition, most of the existing harmful gas reduction technologies are implemented through centralized large-scale reduction facilities, and such large-scale reduction facilities are generally installed in industrial sites where harmful gases are generated in relatively high concentrations, making it difficult to apply the existing technologies directly to the actual living environment of people. Furthermore, pellet or powder-type catalysts are used in large-scale harmful substance removing apparatuses through a simple structure, but development of technologies for miniaturized/commoditized indoor reduction apparatuses is urgently needed in that high costs and periodic replacement are required due to the use of large amount of catalysts.

When plasma and ultraviolet rays are used to remove these harmful substances, an undesired level of residual ozone may be produced. Methods of removing harmful substances may include a filter method, an ultraviolet treatment method, a plasma treatment method, and the like. The filter method generally uses a HEPA filter, but since the HEPA filter must be replaced periodically, there is a risk of infecting an operator during the replacement. The ultraviolet treatment method has a short light absorption distance, and thus when the distance is increased, for example, by about 5 cm, sterilizing power is reduced to less than half, that is, the sterilizing power is insufficient. Also, when ultraviolet rays in the UV-C range are used, there is a possibility of ozone production. The plasma treatment method is excellent in removing harmful substances, but has a limitation that produces residual ozone which is harmful to the human body.

A method of using activated carbon may be used to remove such ozone, but periodic replacement of the activated carbon is required. In addition, a method of removing the ozone by heating the ozone to form oxygen may be used, but there is a limitation in that a high temperature of 300° C. or more is required during simple heating and a separate device is required. Further, a method of removing ozone using a pellet catalyst such as $MnO_2$ may be used, but there is a limitation in that a large amount of catalyst is required and the catalyst must be periodically regenerated or replaced.

DETAILED DESCRIPTION OF THE INVENTION

Technical Problem

The technical problem to be achieved by the technical idea of the present invention is to effectively remove various harmful gases such as volatile organic compounds or ozone, and is to provide a catalyst module for removing harmful gas, wherein an oxidation reaction or reduction reaction of harmful gas is carried out in a self-heating heating carrier, a manufacturing method therefor, and a catalyst system comprising the same for removing harmful gas.

The technical problem to be achieved by the technical idea of the present invention is to provide a harmful substance removing apparatus comprising a catalyst module for removing residual ozone that effectively removes ozone remaining after being used for removing harmful substances, a manufacturing method therefor, and a harmful substance removing system comprising the same.

However, the above technical problems are exemplary, and the scope of the present invention is not limited by these problems.

Technical Solution

According to one aspect of the present invention, there is provided a catalyst module for removing harmful gas.

According to one embodiment of the present invention, the catalyst module for removing harmful gas may include: a heating carrier composed of an electrically heatable heating body, including one or more flow channels inside, and having a porous structure with pores; and a catalyst region formed on at least a portion of the surface of the heating carrier including the flow channels and containing a catalyst material for promoting a decomposition reaction of harmful gas passing through the flow channels, wherein the catalyst region comprises: a first catalyst layer having a first catalyst material loading amount in the pores of the heating carrier; and a second catalyst layer applied on the inner surface of the heating carrier and having a second catalyst material loading amount higher than the first catalyst material loading amount.

According to one embodiment of the present invention, the first catalyst material loading amount may be in the range of, for example, greater than 0 g/L to 50 g/L.

According to an embodiment of the present invention, the second catalyst material loading amount may be in the range of 10 g/L to 220 g/L.

According to one embodiment of the present invention, the first catalyst layer may be applied on the inner surface of the heating carrier, and the second catalyst layer may be applied on a surface of the first catalyst layer.

According to one embodiment of the present invention, the heating carrier may have a porosity in the range of 20% by volume to 70% by volume.

According to one embodiment of the present invention, the catalyst module for removing harmful gas may have a resistance in the range of $0.1\Omega$ to $1000\Omega$.

According to one embodiment of the present invention, the catalyst module for removing harmful gas may further include an electrode connected to a portion of the heating carrier.

According to one embodiment of the present invention, the heating carrier may include at least one of a SiC-based compound, an AlN-based compound, a $BaTiO_3$-based compound, a nickel-chromium-based alloy, an iron-nickel-based alloy, an iron-chromium-based alloy, stainless steel, or a kanthal-based alloy.

According to one embodiment of the present invention, the heating carrier may include a plurality of flow channels extending from one end to an opposite end thereof.

According to one embodiment of the present invention, the heating carrier may include a metal foam.

According to an embodiment of the present invention, the catalyst material may include a metal including at least one of Pt, Pd, Rh, Ru, Fe, Cu, Ni, Mn, Co, Ag, Au, V, Ti, or Mo, a compound containing one or more of the above metals, or an oxide containing one or more of the above metals.

According to an embodiment of the present invention, the catalyst material may include at least one of $MnO_2$, $Mn_2O_3$, MnO, $Mn_3O_4$, $CeO_2$, $TiO_2$, CuO, $V_2O_5$, ZnO, $SnO_2$, $SiO_2$, zeolite, or $Al_2O_3$.

According to one embodiment of the present invention, the catalyst material may further include a doped element.

According to one embodiment of the present invention, the catalyst region may further include a cocatalyst for accelerating catalytic activity and a binder for providing adhesion to the heating carrier.

According to one aspect of the present invention, a catalyst system for removing harmful gas is provided.

According to one embodiment of the present invention, the catalyst system for removing harmful gas may include: the catalyst module for removing harmful gas; a power supply source configured to supply power to the catalyst module for removing harmful gas; and a power control unit configured to control a waveform of the power input from the power supply source to the catalyst module for removing harmful gas.

According to an embodiment of the present invention, the power control unit may further include a temperature control module configured to receive a temperature of the catalyst module for removing harmful gas and control a power value or waveform of the power to be input to the catalyst module for removing harmful gas according to the received temperature.

According to one aspect of the present invention, a manufacturing method of a catalyst module for removing harmful gas is provided.

According to one embodiment of the present invention, the manufacturing method of a catalyst module for removing harmful gas may include: providing a heating carrier composed of an electrically heatable heating body, including one or more flow channels therein, and having a porous structure with pores; forming a first catalyst layer having a first catalyst material loading amount in the pores of the heating carrier; and forming a second catalyst layer applied on an inner surface of the heating carrier and having a second catalyst material loading amount higher than the first catalyst material loading amount.

According to one embodiment of the present invention, the forming of the first catalyst layer may be performed by immersing the heating carrier in a first catalyst solution having the first catalyst material loading amount, or by spraying the first catalyst solution to the heating carrier by means of an air gun.

According to an embodiment of the present invention, the forming of the second catalyst layer may include coating an inner surface of the flow channel with a second catalyst solution by introducing the second catalyst solution having the second catalyst material loading amount and placed outside the flow passage into the flow channel using a pressure difference; and forming the second catalyst layer on the inner surface of the flow channel by drying the coated second catalyst solution.

According to one embodiment of the present invention, the manufacturing method of a catalyst module for removing harmful gas may include: providing a heating carrier composed of an electrically heatable heating body, including one or more flow channels therein, and having a porous structure with pores; filling at least a portion of the pores formed on an inner surface of the flow channel with a fluid; coating the inner surface of the flow channel with a catalyst solution by introducing the catalyst solution placed outside the flow channel into the flow channel by means of a pressure difference; and forming a catalyst layer on the inner surface of the flow channel by drying coated catalyst solution.

According to one aspect of the present invention, a harmful substance removing apparatus including a catalyst module for removing residual ozone is provided.

According to an embodiment of the present invention, the harmful substance removing apparatus may include: a harmful substance removal module; and a catalyst module for removing residual ozone that removes residual ozone generated in the harmful substance removal module, wherein the catalyst module for removing residual ozone may include a heating carrier composed of an electrically heatable heating body, including one or more flow channels therein, and having a porous structure with pores; and a catalyst region formed on at least a portion of the surface of the heating carrier including the flow channels and containing a catalyst material for promoting a decomposition reaction of harmful gas passing through the flow channels, and the catalyst region may include a first catalyst layer having a first catalyst material loading amount in the pores of the heating carrier; and a second catalyst layer applied on the inner surface of the heating carrier and having a second catalyst material loading amount higher than the first catalyst material loading amount.

According to an embodiment of the present invention, the harmful substance removal module and the catalyst module for removing residual ozone may have the same contact cross-sectional areas so that the residual ozone is not discharged to the outside.

According to an embodiment of the present invention, the harmful substance removal module may include a plasma generator configured to generate low-temperature plasma or room-temperature plasma to remove harmful substances.

According to one embodiment of the present invention, the harmful substance removal module may include an ultraviolet ray generator configured to generate ultraviolet rays to remove harmful substances.

According to one embodiment of the present invention, the first catalyst layer may be applied on the inner surface of the heating carrier, and the second catalyst layer may be applied on a surface of the first catalyst layer.

According to one embodiment of the present invention, the first catalyst material loading amount may be in the range of, for example, greater than 0 g/L to 50 g/L, and the second catalyst material loading amount may be in the range of 10 g/L to 220 g/L.

According to one embodiment of the present invention, the heating carrier may have a porosity in the range of 20% by volume to 70% by volume.

According to one embodiment of the present invention, the catalyst module for removing residual ozone may have a resistance in the range of $0.1\Omega$ to $1000\Omega$.

According to one embodiment of the present invention, the harmful substance removing apparatus may further include an electrode connected to a portion of the heating carrier.

According to one embodiment of the present invention, the heating carrier may include at least one of a SiC-based compound, an AlN-based compound, a $BaTiO_3$-based compound, a nickel-chromium-based alloy, an iron-nickel-based alloy, an iron-chromium-based alloy, stainless steel, or a kanthal-based alloy.

According to one embodiment of the present invention, the heating carrier may include a plurality of flow channels extending from one end to an opposite end thereof.

According to one embodiment of the present invention, the heating carrier may include a metal foam.

According to an embodiment of the present invention, the catalyst material may include a metal including at least one of Pt, Pd, Rh, Ru, Fe, Cu, Ni, Mn, Co, Ag, Au, V, Ti, or Mo, a compound containing one or more of the above metals, or an oxide containing one or more of the above metals.

According to an embodiment of the present invention, the catalyst material may include at least one of $MnO_2$, $Mn_2O_3$, MnO, $Mn_3O_4$, $CeO_2$, $TiO_2$, CuO, $V_2O_5$, ZnO, $SnO_2$, $SiO_2$, zeolite, or $Al_2O_3$.

According to one embodiment of the present invention, the catalyst material may further include a doped element.

According to one embodiment of the present invention, the catalyst region may further include a cocatalyst for accelerating catalytic activity and a binder for providing adhesion to the heating carrier.

According to an embodiment of the present invention, the harmful substance removal module may remove harmful substances using plasma or ultraviolet rays.

According to one aspect of the present invention, a harmful substance removing system is provided.

According to one embodiment of the present invention, the harmful substance removing system may include: the harmful substance removing apparatus; a power supply source configured to supply power to the catalyst module for removing residual ozone of the harmful substance removing apparatus; and a power control unit configured to control a waveform of the power input from the power supply source to the catalyst module for removing residual ozone of the harmful substance removing apparatus.

According to an embodiment of the present invention, the power control unit may further include a temperature control module configured to receive a temperature of the catalyst module for removing residual ozone and control a power value or waveform of the power to be input to the catalyst module for removing residual ozone according to the received temperature.

According to one aspect of the present invention, a manufacturing method of a harmful substance removing apparatus is provided.

According to an embodiment of the present invention, the manufacturing method of a harmful substance removing apparatus may be a manufacturing method of a harmful substance removing apparatus including a harmful substance removal module and a catalyst module for removing residual ozone that removes residual ozone generated in the harmful substance removal module, wherein the catalyst module for removing residual ozone may be formed by a method including: providing a heating carrier composed of an electrically heatable heating body, including one or more flow channels therein, and having a porous structure with pores; forming a first catalyst layer having a first catalyst material loading amount in the pores of the heating carrier; and forming a second catalyst layer applied on an inner surface of the heating carrier and having a second catalyst material loading amount higher than the first catalyst material loading amount.

According to one embodiment of the present invention, the forming of the first catalyst layer may be performed by immersing the heating carrier in a first catalyst solution having the first catalyst material loading amount, or by spraying the first catalyst solution to the heating carrier by means of an air gun.

According to an embodiment of the present invention, the forming of the second catalyst layer may include coating an inner surface of the flow channel with a second catalyst solution by introducing the second catalyst solution having the second catalyst material loading amount and placed outside the flow passage into the flow channel using a pressure difference; and drying the coated second catalyst solution to form the second catalyst layer on the inner surface of the flow channel.

According to an embodiment of the present invention, the manufacturing method of a harmful substance removing apparatus may be a manufacturing method of a harmful substance removing apparatus including a harmful substance removal module and a catalyst module for removing residual ozone that removes residual ozone generated in the harmful substance removal module, wherein the catalyst module for removing residual ozone may be formed by a method including: providing a heating carrier composed of an electrically heatable heating body, including one or more flow channels therein, and having a porous structure with pores; filling at least a portion of the pores formed on an inner surface of the flow channel with a fluid; coating the inner surface of the flow channel with a catalyst solution by introducing the catalyst solution placed outside the flow channel into the flow channel by means of a pressure difference; and forming a catalyst layer on the inner surface of the flow channel by drying coated catalyst solution.

Advantageous Effects

According to the technical idea of the present invention, a catalyst module for removing harmful gas is configured to include a heating carrier having a porous structure with pores, a first catalyst layer formed in the pores, and a second coating layer applied on an inner surface of the heating carrier, so that the surface area of a catalyst region is increased, making it possible to more efficiently remove harmful gas.

In addition, since an additional heating device is not required, high efficiency of heat energy use and excellent heat exchange efficiency between catalyst and gas may be achieved, and miniaturization/commoditization of a harmful gas removing system at low cost may be realized by compactly arranging or integrating a catalyst module. Harmful gas components can be directly oxidized without using an additional adsorbent, and even room-temperature harmful gases can be removed since the temperature of the gases can be raised through self-heating.

The heating of the heating carrier is not by an external heat source, but by the electrical resistance of the heating carrier itself, and therefore, in the embodiment of the present invention, as compared to the case where heating is performed by heat energy input from the outside, a response to temperature change according to the power input is remarkably fast. In addition, a process of decomposing harmful gas is repeated within a short time by repeatedly inputting power of a pulse waveform, thereby effectively processing the harmful gas within the short period of time.

According to the technical idea of the present invention, a harmful substance removing apparatus is configured to include a heating carrier having a porous structure with pores, a first catalyst layer formed in the pores, and a second catalyst layer applied on an inner surface of the heating carrier, so that the surface area of a catalyst region is increased, making it possible to more efficiently remove harmful gas.

In addition, since an additional heating device is not required, high efficiency of heat energy use and excellent heat exchange efficiency between catalyst and gas may be achieved, and miniaturization/commoditization of a residual gas removing system at low cost may be realized by compactly arranging or integrating a catalyst module. Residual ozone can be directly decomposed without using an additional adsorbent, and even room-temperature residual ozone can be removed since the temperature of a gas can be raised through self-heating.

The heating of the heating carrier is not by an external heat source, but by the electrical resistance of the heating carrier itself, and therefore, in the embodiment of the present invention, as compared to the case where heating is performed by heat energy input from the outside, a response to temperature change according to the power input is remarkably fast. In addition, a process of decomposing residual gas is repeated within a short time by repeatedly inputting power of a pulse waveform, thereby effectively processing the residual ozone within the short period of time.

The above effects of the present invention have been described as examples, and the scope of the present invention is not limited by these effects.

MODE FOR CARRYING OUT THE INVENTION

Figure 1:
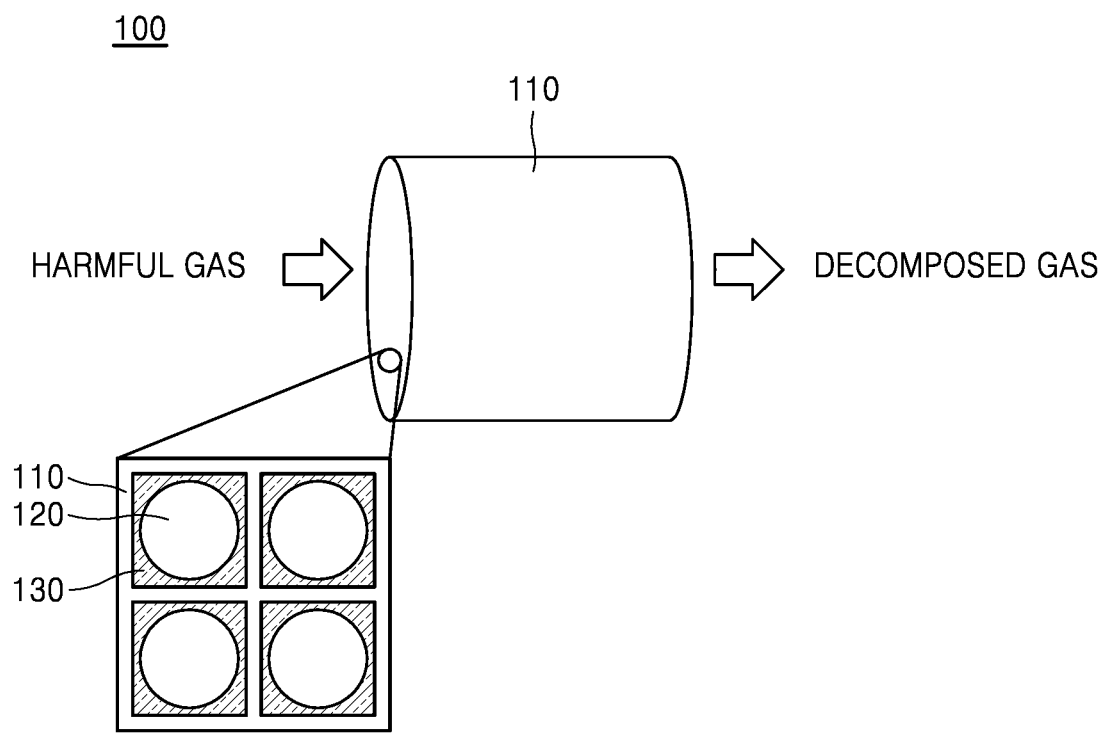
FIG. 1 is a schematic diagram illustrating a catalyst module for removing harmful gas according to an embodiment of the present invention.

Hereinafter, preferred embodiments of the present invention will be described in detail with reference to the accompanying drawings. The embodiments of the present invention are provided for more fully describing the present invention to those skilled in the art, and the embodiments below may be modified in various forms, and the scope of the present invention is not limited to the embodiments below. Rather, these embodiments are provided such that this disclosure will be thorough and complete and will fully convey the spirit of the present invention to those skilled in the art. Like numbers refer to like elements throughout. Furthermore, various elements and regions in the drawings are schematically shown. Thus, the technical idea of the present invention is not limited by a relative size or distance in the attached drawings.

Catalyst Module for Removing Harmful Gas

FIG. 1 is a schematic diagram illustrating a catalyst module 100 for removing harmful gas according to an embodiment of the present invention.

Referring to FIG. 1, the catalyst module 100 for removing harmful gas includes a heating carrier 110 and a catalyst region 130.

The heating carrier 110 may be composed of an electrically heatable heating body, may include one or more flow channels 120 therein, through which a fluid can flow, and may have a porous structure having a plurality of pores. The heating carrier 110 may include a plurality of flow channels 120 extending from one end to the opposite end thereof.

One end of the flow channel 120 may be an inlet through which a fluid is introduced, and the opposite end may be an outlet through which the fluid is discharged. The heating carrier 110 may be formed of a plurality of flow channels having a rectangular cross section that are adjacent to each other from one end to the opposite end. As another example, the flow channels may be in the shape of a honeycomb having a regular hexagonal cross section. In addition, there is no particular limitation on the cross-sectional shape of the flow channel, such as a triangle or a circle, and any shape is possible as long as the flow channel can flow a fluid into the heating carrier 110. As another example of the structure of the heating carrier 110, the heating carrier 110 may have a plurality of empty spaces therein, and may include a porous material, for example, a porous metal, in which the empty spaces are connected to each other to form a flow channel.

The heating carrier 110 is composed of an electric heating body capable of being self-heated by electrical resistance when electric power is applied thereto. For example, a conductive ceramic or metal material may be used as the material of the heating carrier 110. The conductive ceramic material may include a SiC-based compound, an AlN-based compound, a $BaTiO_3$-based compound, and the like. The metal material may include, for example, nickel-chromium-based alloys, iron-nickel-based alloys, iron-chromium-based alloys, stainless steel, kanthal-based alloys, and the like.

The fluid may include harmful gases to be removed. The harmful gases may include at least one of, for example, volatile organic compounds (VOCs), nitrogen oxides (NOx) that are exhausted from vehicles or boilers and cause greenhouse effects and acid rain, various odors, various hydrocarbons (CxHy), carbon monoxide (CO), ozone, harmful radicals, pathogens, or viruses. However, these are exemplary and the technical idea of the present invention is not limited thereto.

The catalyst region 130 is formed on at least a portion of the surface of the heating carrier 110 provided with the flow channels 120 and includes a catalyst material that promotes the decomposition reaction of the harmful gases passing through the flow channels 120. The catalyst material used in the catalyst region 130 may include a metal including at least one of Pt, Pd, Rh, Ru, Fe, Cu, Ni, Mn, Co, Ag, Au, V, Ti and Mo, a compound containing one or more of the above metals, or an oxide containing one or more of the above metals. The oxide may include at least one of $MnO_2$, $Mn_2O_3$, MnO, $Mn_3O_4$, $CeO_2$, $TiO_2$, CuO, $V_2O_5$, ZnO, $SnO_2$, $SiO_2$, zeolite, or $Al_2O_3$. The catalyst material may further include a doped element. For example, the catalyst material may include $Ce_{1-x}Zr_xO_2$ in which $CeO_2$ is doped with zirconium, which is another element. In addition, the catalyst region 130 may further include a metal or oxide cocatalyst that accelerates catalytic activity. In addition, the catalyst region 130 may further include a binder that provides adhesion to the heating carrier 110. The binder may include, for example, an aluminum compound (boehmite), $SiO_2$, $TiO_2$, a clay-based material, and the like. The catalyst region 130 will be described in detail below.

An electrode structure (not shown) to which electric power can be applied from the outside is formed on the heating carrier 110. The electrode structure may be formed on the side or on the front and rear ends of the heating carrier 110. For example, the electrode structure connected to an external power line may be formed by coating specific regions of one end and the opposite end of the heating carrier 110 respectively with a conductive paste. As another example, the electrode structure may be formed by bonding conductive metal members to specific regions of one end and the opposite end of the heating carrier 110, respectively. The catalyst module 100 for removing harmful gas may have a resistance in the range of, for example, 0.1Ω to 1000Ω, for example, 0.5Ω to 500Ω, or, for example, 1Ω to 100Ω The resistance may vary depending on the size of the catalyst module 100 for removing harmful gas. The resistance is mainly found in the heating carrier 110 constituting the catalyst module 100 for removing harmful gas, and heating is induced according to the resistance.

Figure 2:
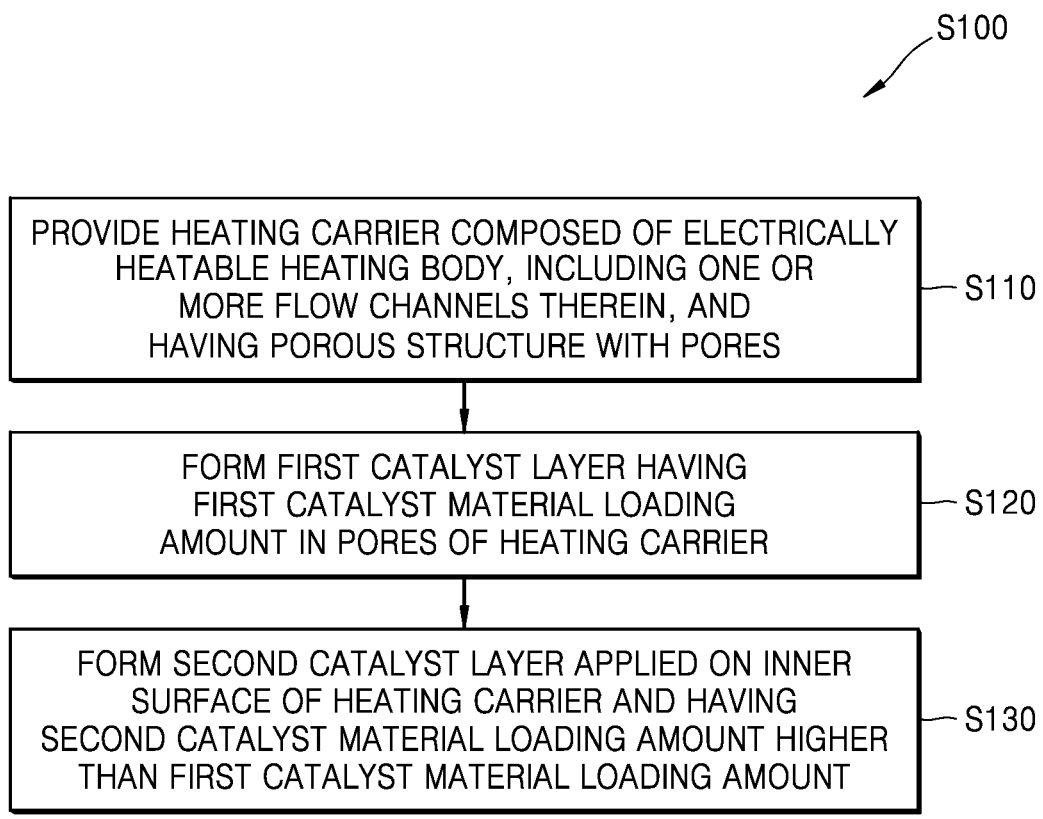
FIG. 2 is a flowchart illustrating a manufacturing method of a catalyst module for removing harmful gas according to an embodiment of the present invention.

FIG. 2 is a flowchart illustrating a manufacturing method (S100) of a catalyst module for removing harmful gas according to an embodiment of the present invention.

Referring to FIG. 2, the manufacturing method (S100) of a catalyst module for removing harmful gas may include providing a heating carrier that is composed of an electrically heatable heating body, includes one or more flow channels therein, and has a porous structure with pores (S110); forming a first catalyst layer having a first catalyst material loading amount in the pores of the heating carrier (S120); and forming a second catalyst layer applied on an inner surface of the heating carrier and having a second catalyst material loading amount higher than the first catalyst material loading amount (S130).

Figure 3:
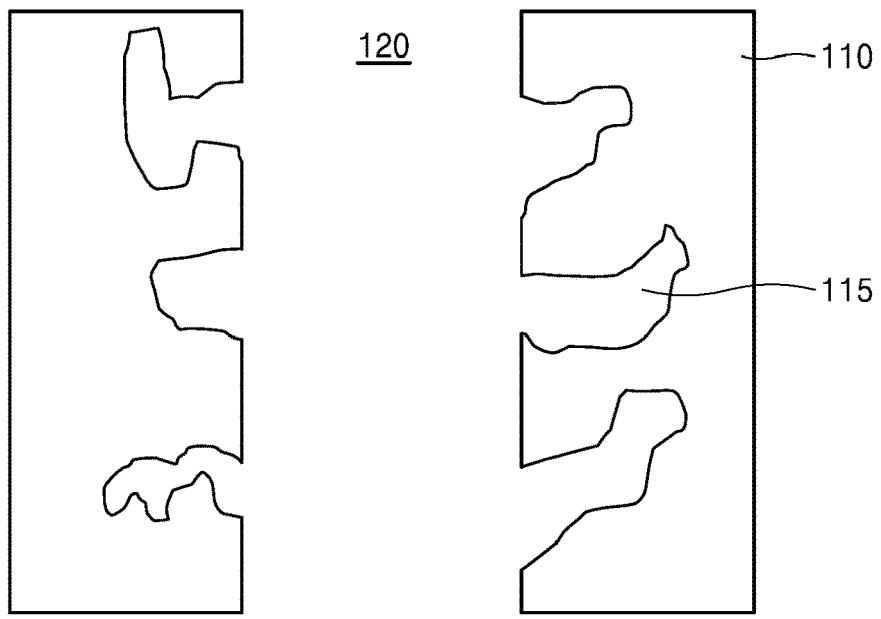
FIGS. 3 to 5 are schematic diagrams illustrating processes of manufacturing a catalyst module for removing harmful gas according to an embodiment of the present invention.
Figure 4:
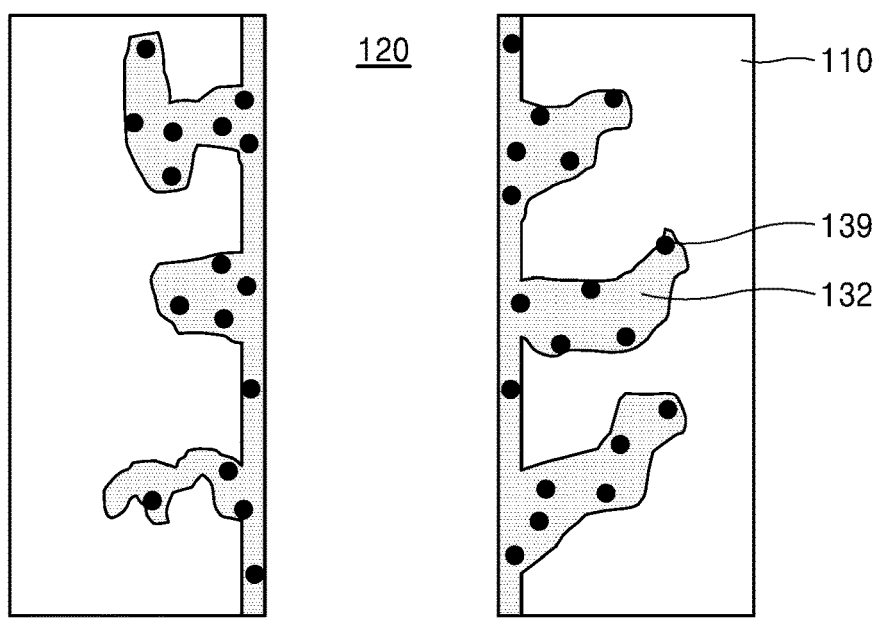
Figure 5:
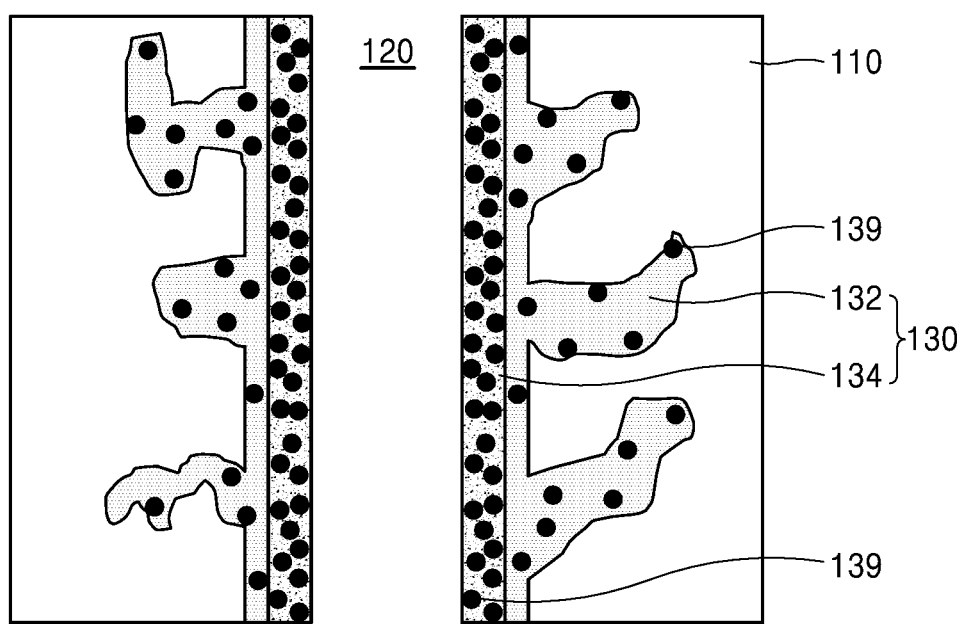

FIGS. 3 to 5 are schematic diagrams illustrating processes of manufacturing a catalyst module 100 for removing harmful gas according to an embodiment of the present invention.

Referring to FIGS. 2 and 3, the heating carrier 110 may be formed to include a plurality of pores 115. The heating carrier 110 may have a porosity in the range of, for example, 20 vol % to 70 vol %, and may have a porosity in the range of, for example, 30 vol % to 60 vol %. The pores 115 may open toward the flow channel 120.

Referring to FIGS. 2 and 4, a first catalyst layer 132 filled in at least part of the pores 115 of the heating carrier 110 is formed. In addition, the first catalyst layer 132 may be further applied on the inner surface of the heating carrier 110 to make contact with the inner surface of the heating carrier 110.

The first catalyst layer 132 may further include the catalyst material 139 as described above. The first catalyst layer 132 may have a first catalyst material loading amount. The first catalyst material loading amount may be expressed as the weight of a first catalyst material relative to the total apparent volume of the heating carrier 110. The apparent volume as used herein means the total volume of the heating carrier in appearance when the flow channels and the pores are assumed to be filled such that the empty space due to the flow channels and pores inside the heating carrier 110 is to be neglected.

The first catalyst material loading amount means the amount of the first catalyst material contained in the heating carrier 110. The first catalyst material loading amount may be in the range of, for example, greater than 0 g/L to 50 g/L. That is, the first catalyst material loading amount may be 50 g or less of the first catalyst material with respect to the apparent volume of the heating carrier 110 of 1 L. Alternatively, the first catalyst material loading amount may be expressed as the coating amount of the first catalyst material coated onto the interior of the heating carrier 110.

The forming of the first catalyst layer 132 may be performed by immersing the heating carrier 110 in a first catalyst solution having the first catalyst material loading amount, or by spraying the first catalyst solution to the heating carrier 110 by means of an air gun.

The first catalyst solution may have a slurry form. The concentration of the first catalyst material in the first catalyst solution may be in the range of greater than 0 wt % to 20 wt % or less based on the total weight of the first catalyst solution.

Referring to FIGS. 2 and 5, a second catalyst layer 134 applied on the inner surface of the heating carrier 110 is formed. The second catalyst layer 134 may be applied to make contact with the inner surface of the heating carrier 110 or may be applied on the surface of the first catalyst layer 132.

The second catalyst layer 134 may further include the catalyst material 139 as described above. The catalyst material 139 included in the first catalyst layer 132 may be the same as or different from the catalyst material 139 included in the second catalyst layer 134. The second catalyst layer 134 may have a second catalyst material loading amount. The second catalyst material loading amount may be expressed as the weight of a second catalyst material relative to the total apparent volume of the heating carrier 110. The second catalyst material loading amount means the amount of the second catalyst material contained in the heating carrier 110. The second catalyst material loading amount may be in the range of, for example, 10 g/L to 220 g/L. That is, the second catalyst material loading amount may be greater than 10 g to 200 g or less of the second catalyst material with respect to the apparent volume of the heating carrier 110 of 1 L. Alternatively, the second catalyst material loading amount may be expressed as the coating amount of the second catalyst material coated onto the interior of the heating carrier 110.

The forming of the second catalyst layer 134 may include coating the inner surface of the flow channel with a second catalyst solution by introducing the second catalyst solution having the second catalyst material loading amount and placed outside the flow passage 120 into the flow channel 120 using a pressure difference; and drying the coated second catalyst solution to form the second catalyst layer 134 on the inner surface of the flow channel 120.

Specifically, the forming of the second catalyst layer 134 may be performed by bringing one end of the heating carrier 110 into contact with the second catalyst solution having the second catalyst material loading amount and sucking the second catalyst solution into the heating carrier by means of a pressure difference caused by reducing pressure of the opposite end of the heating carrier 110. The reduction of pressure may cause a pressure difference between the one end and the opposite end such that the second catalyst solution may be sucked into the heating carrier through the flow channel 120. The reduction of pressure may be carried out using a vacuum pump.

The second catalyst solution may have a slurry form. The concentration of the second catalyst material in the second catalyst solution may be in the range of greater than 10 wt % to 60 wt % or less based on the total weight of the second catalyst solution.

In addition, the catalyst module for removing harmful gas may be manufactured using a fluid such as water that does not contain a catalyst material, instead of the first catalyst solution. In this case, the fluid may be filled in the pores formed in the heating carrier 110 and a target pressure difference may be maintained between the one end and the opposite end, so that the second catalyst solution may be easily introduced into the flow channel 120.

Figure 6:
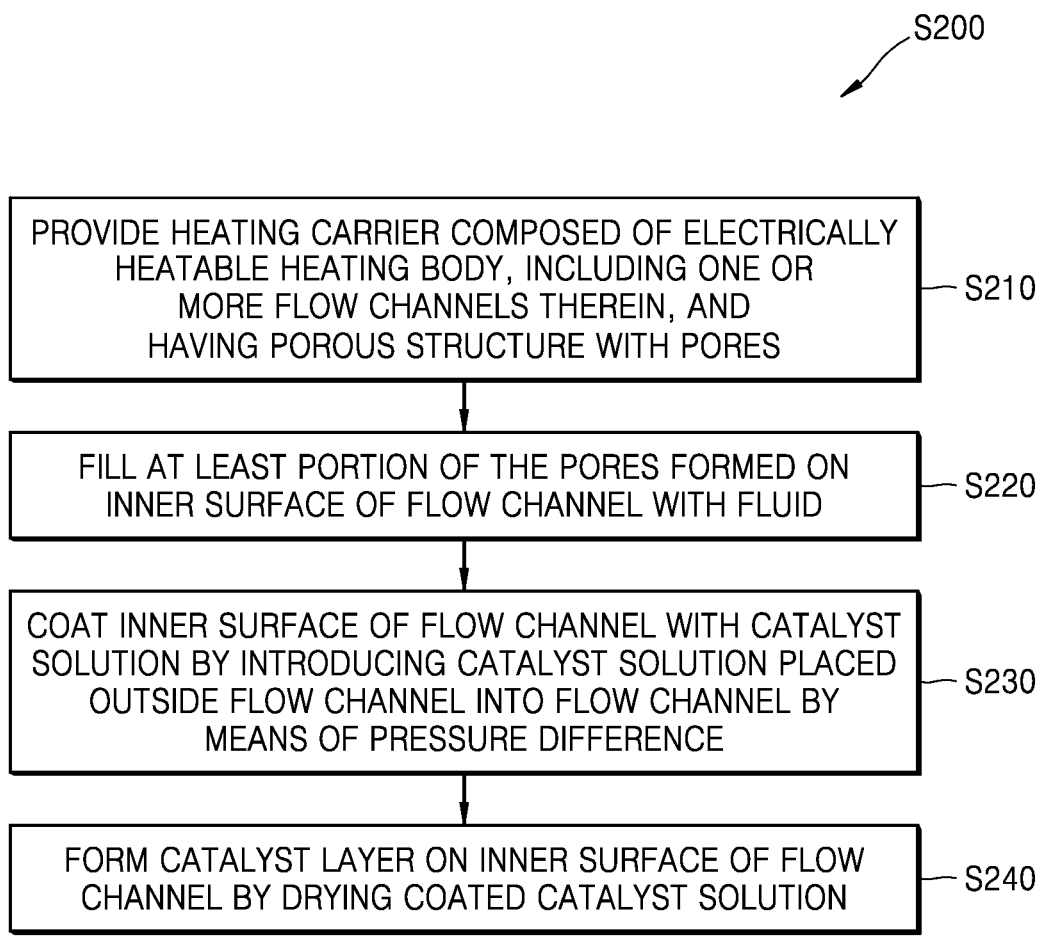
FIG. 6 is a flowchart illustrating a manufacturing method of a catalyst module for removing harmful gas according to an embodiment of the present invention.

FIG. 6 is a flowchart illustrating a manufacturing method (S200) of a catalyst module for removing harmful gas according to an embodiment of the present invention.

Referring to FIG. 6, the manufacturing method (S200) of a catalyst module for removing harmful gas includes providing a heating carrier 110 that is composed of an electrically heatable heating body, includes one or more flow channels 120 therein, and has a porous structure with pores 115 (S210); filling at least a portion of the pores 115 formed on an inner surface of the flow channel 120 with a fluid (S220); coating the inner surface of the flow channel 120 with a catalyst solution by introducing the catalyst solution placed outside the flow channel 120 into the flow channel 120 by means of a pressure difference (S230); and forming a catalyst layer on the inner surface of the flow channel 120 by drying the coated catalyst solution (S240).

The fluid filled in the pores 115 may include water. In this case, the fluid may not include the same catalyst material as contained in the catalyst solution. In some cases, the catalyst material contained in the catalyst solution may be moved to the fluid filled in the pores 115 by diffusion or the like.

Figure 7:
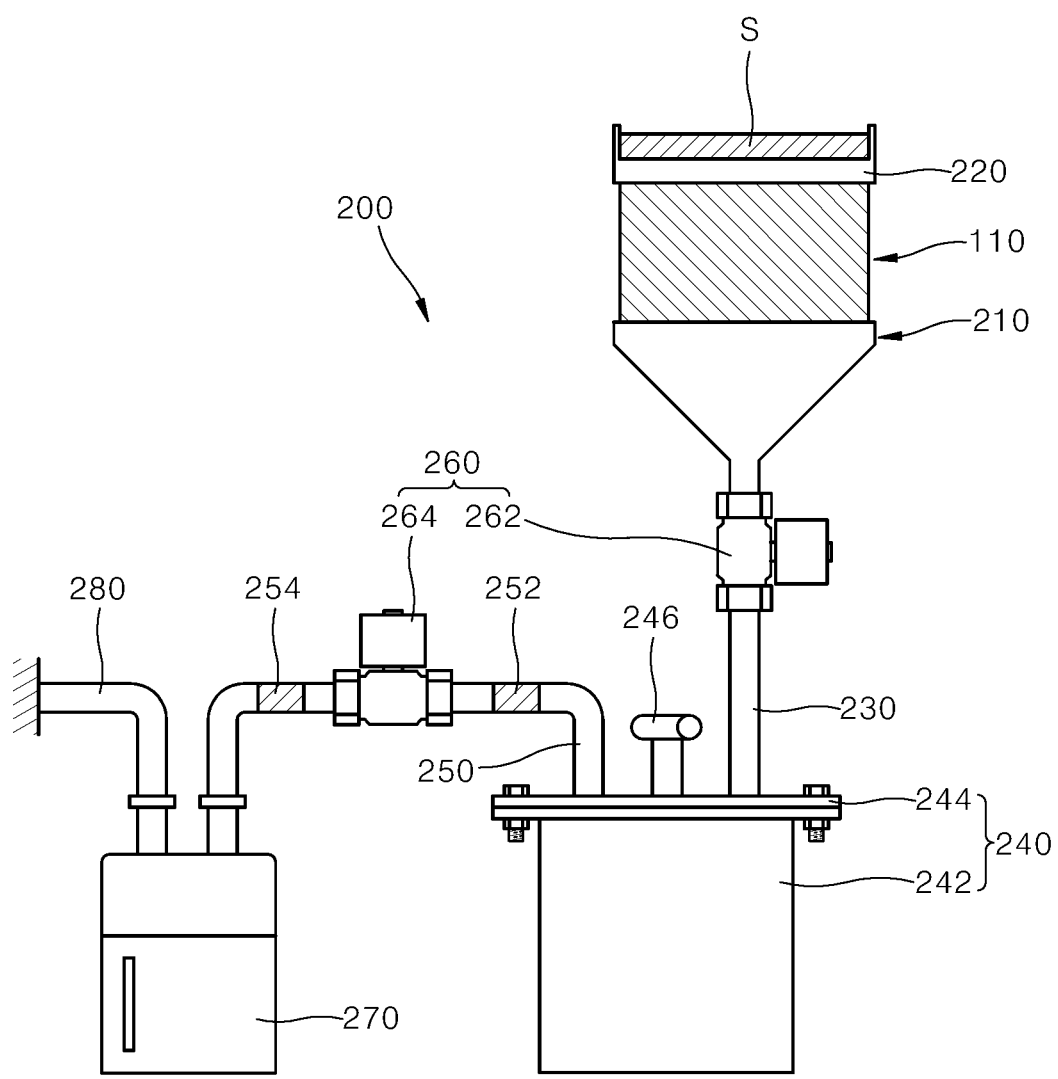
FIG. 7 is a schematic view illustrating an apparatus for manufacturing a catalyst module for removing harmful gas that performs a manufacturing method of a catalyst module for removing harmful gas according to an embodiment of the present invention.

FIG. 7 is a schematic view illustrating an apparatus 200 for manufacturing a catalyst module for removing harmful gas that performs a manufacturing method of a catalyst module for removing harmful gas according to an embodiment of the present invention.

Referring to FIG. 7, the apparatus 200 for manufacturing a catalyst module for removing harmful gas is an apparatus that enables catalyst coating by tightly fixing a heating carrier 110 requiring a catalyst coating process, creating a vacuum atmosphere in an inner space, and then allowing a slurry S, which corresponds to a second catalyst solution, to penetrate into the heating carrier 110 due to a pressure difference caused by releasing the vacuum atmosphere. To this end, the apparatus 200 for manufacturing a catalyst module for removing harmful gas is configured to include a rack 210 in which the heating carrier 110 is tightly fixed, a hopper 220 configured to store the slurry S and selectively supply the slurry S to the heating carrier 110, a supply pipe 230 configured to communicate with the rack 210 and guide a flow direction of the slurry S passing through the heating carrier 110 and the rack 210, a chamber 240 configured to store the slurry S that has sequentially passed through the heating carrier 110 and the supply pipe 230, a discharge pipe 250 configured to selectively discharge a gas inside the chamber 240, a valve 260 configured to selectively close the supply pipe 230 and the exhaust pipe 250, a vacuum pump 270 configured to create a vacuum atmosphere inside the chamber 240 according to whether the valve 260 is open, an exhaust pipe 280 configured to exhaust the gas passing through the vacuum pump 270 to the outside, and a control unit 290 configured to control the operation of the valve 260 and the vacuum pump 270.

Most of the above components are embedded in a case (not shown) of a rectangular parallelepiped shape with an empty inside, and the rack 210 and the hopper 220 are exposed to an upper side of the case. That is, the rack 210 is formed on an upper surface of the case to have a tubular shape penetrating through the interior of the case and the heating carrier 110 is seated and fixed onto the rack 210.

Although the heating carrier 110 is formed of ceramic in an embodiment of the present invention, various materials may be applied to the heating carrier 110.

The rack 210 is configured such that the shape of an open upper portion thereof corresponds to the outer shape of the heating carrier 110, thereby accommodating the heating carrier 110 therein, and the interior of the heating carrier 110 inserted into the rack 210 communicates with the interior of the rack 210. The hopper 220 is provided on an upper side of the heating carrier 110. The hopper 220 is configured to form a space in which the slurry S containing the catalyst material is stored, and is configured so that a lower portion thereof can be tightly coupled to the upper side of the heating carrier 110 as in the rack 210, and the upper portion of the hopper 220 is recessed to a predetermined depth and hence is enabled to store the slurry S. In addition, an open upper space of the hopper 220 is directed downward so that the slurry (S) stored in the upper portion can flow into the heating carrier 110.

The supply pipe 230 is provided in the lower portion of the rack 210. The supply pipe 230 is configured to create a path for the slurry S stored in the hopper 220 to move after passing through the interior of the heating carrier 110 and the rack 210, and is coupled to communicate with the interior of the chamber 240. Therefore, the slurry S remaining after being coated while passing through the heating carrier 110 is introduced into the chamber 240 through the supply pipe 230, so that it can be stored in the chamber 240.

The chamber 240 is configured to store an excessive slurry S and to selectively discharge the slurry S. Specifically, the chamber 240 includes a container portion 242 having a container shape to store the slurry S and a closing portion 244 for selectively closing the container portion 242. In an embodiment of the present invention, the container portion 242 is configured to be easily detachable from the closing portion 244, and the supply pipe 230 is connected to the closing portion 244 and guides the slurry S to the inner space of the container 242 when the closing portion 244 and the container portion 242 are coupled to each other in a sealed state.

The discharge pipe 250 is provided in one direction of the chamber 240. The discharge pipe 250 is configured to be coupled to communicate with the inner space of the chamber 240 so that the gas inside the chamber 240 can be discharged to the outside. That is, the discharge pipe 250 is configured to selectively discharge the gas when the slurry S and the external gas are introduced into the chamber 240.

The chamber 240 is configured such that a vacuum atmosphere can be selectively created by the action of the valve 260 and the vacuum pump 270 described above. That is, a first valve 262 is provided on one side of the supply pipe 230 and a second valve 264 is provided on one side of the discharge pipe 250 so that the chamber 240 can be sealed by closing the supply pipe 230 and the discharge pipe 250 by the operation of the first valve 262 and the second valve 264. When the vacuum pump 270 operates with only the discharge pipe 250 open, a vacuum atmosphere may be created inside the chamber 240. In addition, the first valve 262 and the second valve 264 are configured to be open or closed for a preset time with a built-in timer function. Also, the first valve 262 and the second valve 264 are configured to be selectively controlled by the control unit so that the opening degrees thereof can be adjusted. This is to prevent the formation of an excessive vacuum atmosphere inside the chamber 240 when the vacuum pump 270 operates.

A first filter 252 and a second filter 254 are built into one side of the discharge pipe 250. The first filter 252 and the second filter 254 are configured to filter out oil or foreign substances that may be discharged from the interior of the chamber 240 through the discharge pipe 250 and to prevent the oil or foreign substances from flowing into the vacuum pump 270. That is, the first filter 252 is located adjacent to the chamber 240 and serves to remove foreign substances in the air discharged from the interior of the chamber 240, and the second filter 254 is disposed adjacent to the vacuum pump 270 to remove oil that may flow into the vacuum pump 270.

Meanwhile, a pressure sensor 246 is provided on one side of the chamber 240, i.e., in the closing portion 244. The pressure sensor 246 is configured to measure a pressure of the vacuum atmosphere created inside the chamber 240 and serves to provide the measured pressure to the control unit.

The apparatus 200 for manufacturing a catalyst module for removing harmful gas may further include a control unit (not shown), wherein the control unit is configured to control the operation of the vacuum pump 270 by comparing the degree of vacuum inside the chamber 240 received from the pressure sensor 246 with a preset value and also to enable to perform the overall operation of the apparatus 200 by setting the opening degrees and opening time of the first valve 262 and the second valve 264.

Hereinafter, a method of coating the heating carrier 110 with a catalyst material using the apparatus 200 for manufacturing a catalyst module for removing harmful gas will be described.

First, the heating carrier 110 is tightly fixed to the rack 210 and a slurry S is prepared in the hopper 220 for supplying the slurry S containing a catalyst material to the heating carrier 110. In this process, the heating carrier 110, the slurry S, and the like are prepared and set in the apparatus 200 for manufacturing a catalyst module for removing harmful gas, wherein the heating carrier 110 is seated such that the interior thereof communicates with the interior of the rack 210, the hopper 220 is seated on the upper portion of the heating carrier 110, and the slurry S is injected into the hopper 220 and stored. In addition, the interior of the rack 210 is disconnected from the interior of the chamber 240. That is, the interior of the supply pipe 230 is closed by operating the first valve 262 and the chamber 240 and the second valve 264 is opened to prepare the chamber 240 and the vacuum pump 270 to communicate with each other.

Thereafter, a vacuum atmosphere is created inside the chamber 240 configured to store the slurry S passing through the heating carrier 110. In this process, the vacuum pump 270 is operated to generate a suction force and the suction force is transferred to the chamber 240 through the discharge pipe 250, thereby forcing the vacuum atmosphere to be created inside the chamber 240. At this time, the discharge pipe 250 is selectively closed so that the degree of vacuum inside the chamber 240 can be maintained constant. That is, the degree of vacuum inside the chamber 240 is raised by the operation of the vacuum pump 270, and when the degree of vacuum reaches a preset specific vacuum degree range, the pressure sensor 246 detects the degree of vacuum and notifies it to the control unit so that the control unit closes the second valve 264 to maintain the degree of vacuum inside the chamber 240. At the same time, the control unit preferably cuts off a power supply applied to the vacuum pump 270.

Then, the vacuum atmosphere is released by opening the interior of the chamber 240 and the heating carrier 110 so that the slurry S passes through the interior of the heating carrier 110 and is thus coated onto the heating carrier 110. In this process, the catalyst material is substantially coated onto the interior of the heating carrier 110 and this process is completed by opening the supply pipe 230. More specifically, since a vacuum atmosphere is created in the chamber 240, the chamber 240 provides the suction force to the supply pipe 230, the rack 210, and the heating carrier 110 when the first valve 262 is opened, and this suction force draws the slurry S into the heating carrier 110. A part of the slurry S drawn into the heating carrier 110 is coated onto the wall while passing through the interior of the heating carrier 110, and the rest of the slurry S that is not coated flows down along the rack 210 and the supply pipe 230 and enters into and is stored in the chamber 240. Accordingly, the slurry S can be coated onto the interior of the heating carrier 110 by an instantaneous opening operation of the first valve 262.

After the above process, the coating of the catalyst material is completed, then the second valve 264 is opened, the first valve 262 is closed, and the vacuum pump 270 is operated until the pressure inside of the chamber 240 reaches a value within a set pressure range. Along with this process, a vacuum is formed inside the chamber 240 again. Of course, before forming the vacuum again, one surface of another heating carrier 110 requiring coating is seated on the rack 210, and the hopper 220 is seated on the other surface of the heating carrier 110 to prepare for coating of the catalyst material.

Figure 8:
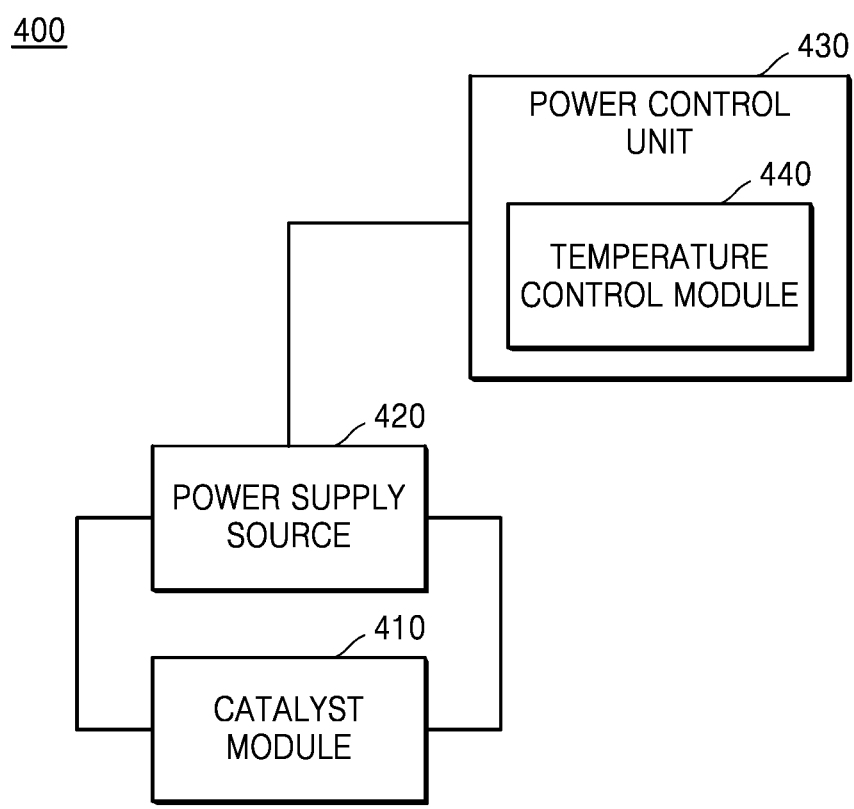
FIG. 8 is a schematic diagram illustrating a catalyst system for removing harmful gas that is constructed using a catalyst module for removing harmful gas according to an embodiment of the present invention.

FIG. 8 is a schematic diagram illustrating a catalyst system 400 for removing harmful gas that is constructed using a catalyst module for removing harmful gas according to an embodiment of the present invention.

Referring to FIG. 8, the catalyst system 400 for removing harmful gas includes a catalyst module 410 for removing harmful gas, a power supply source 420 configured to supply power to the catalyst module 410 for removing harmful gas, and a power control unit 430 configured to control the power input to the catalyst module 410 for removing harmful gas. The power control unit 430 may control, for example, a power value or a waveform of the power supplied.

The power control unit 430 may further include a temperature control module 440 configured to receive a temperature of the catalyst module 410 for removing harmful gas and control a power value or waveform of the power to be input to the catalyst module 410 for removing harmful gas according to the received temperature.

The power from the power supply source 420 may be controlled to be supplied to the heating carrier constituting the catalyst module 410 for removing harmful gas under the control of the power control unit 430. The heating carrier supplied with the power may be self-heated, and at this time, the input power value or waveform may be controlled by the power control unit 430 so that the temperature of the self-heating heating carrier can be maintained within a predetermined range.

Figure 9:
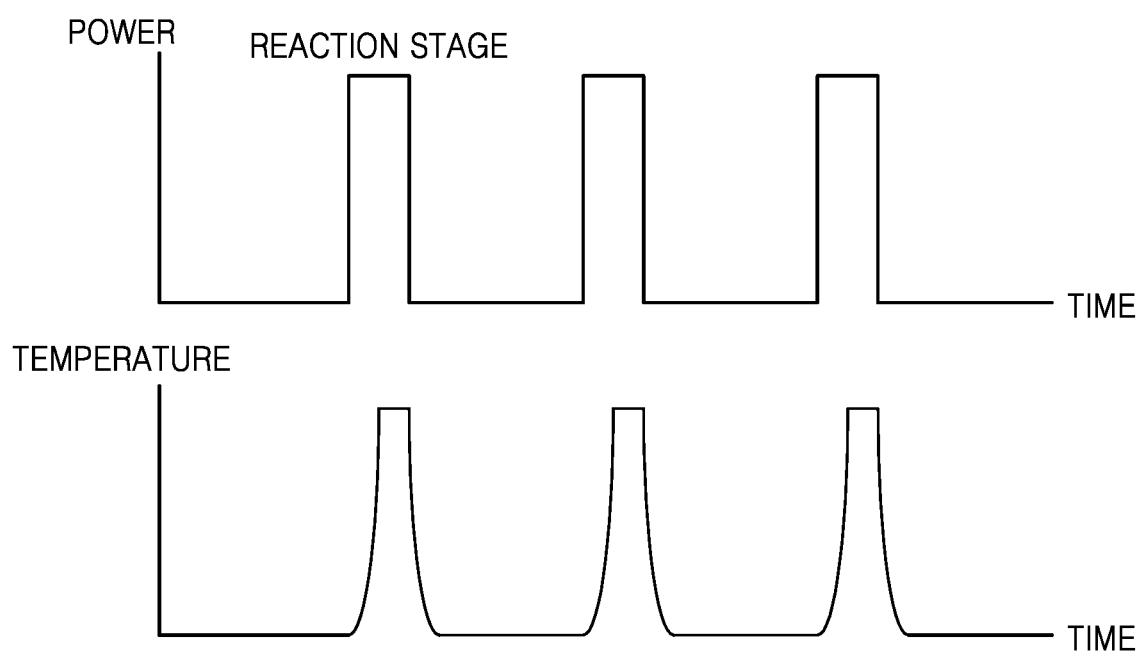
FIG. 9 is a graph illustrating an operating method of the catalyst system for removing harmful gas of FIG. 8 according to an embodiment of the present invention.

FIG. 9 is a graph illustrating an operating method of the catalyst system 400 for removing harmful gas of FIG. 8 according to an embodiment of the present invention.

Referring to FIG. 9, an operating method of the catalyst system 400 for removing harmful gas according to the temporal order in which power is supplied to the heating carrier 110 constituting the catalyst module 410 for removing harmful gas is shown. Specifically, the pulse-shaped waveform of the power applied to the heating carrier 110 and the corresponding temperature change of the heating carrier 110 are shown.

A method of removing harmful gas using the catalyst system 400 for removing harmful gas will be described with reference to FIGS. 1 to 9.

When power is supplied to the heating carrier 110, the heating carrier 110 may be self-heated. The temperature of the heating carrier 110 may be rapidly raised and maintained within an operating range in which a catalyst can efficiently operate by a predetermined power supply value.

In the catalyst system 400 for removing harmful gas according to an embodiment of the present invention, the heating of the heating carrier 110 is realized by self-heating of the heating carrier 110, which is an electrical resistance heating body, rather than by an external heat source. That is, electric power is directly applied to the heating carrier 110 to heat the heating carrier 110. Therefore, as compared to the conventional heating by heat energy input from an external source, a response to temperature change according to power input is remarkably fast. Accordingly, it is possible to rapidly heat the heating carrier 110 by controlling the waveform of the power input to the heating carrier 110. For example, when power in the form of a pulse is supplied to the heating carrier 110 for a short time through the power supply unit 430, the heating carrier 110 also exhibits a temperature change in the form of a pulse.

Meanwhile, the heating carrier 110 may be rapidly heated when power in the form of a pulse is applied, and may also be rapidly cooled at a room temperature or in a cold air when the applied power is removed. For example, the catalyst module is cooled back to the temperature before it was heated and then waits until it is heated.

A harmful gas is introduced into the flow channel 120 of the heated heating carrier 110 and then flows along the flow channel of the heating carrier 110. During this process, the harmful gas may be decomposed while the decomposition reaction is accelerated by the catalyst region 130. This process corresponds to "reaction stage" shown in FIG. 9. For example, when the harmful gas is a volatile organic compound, the harmful gas is decomposed into carbon dioxide ($CO_2$) gas and water vapor ($H_2O$) while the oxidation reaction is accelerated in the catalyst region 130, and is discharged to the outside through the flow channel 120 at the opposite end of the heating carrier 110.

Hereinafter, an experimental example of a catalyst module for removing harmful gas according to the technical idea of the present invention will be described.

As experimental conditions of the catalyst module for removing harmful gas, a voltage of 30V to 50V, a current of 20 A, a space velocity (GHSV) of 12,000/h, and a heating carrier with a cross-sectional area of 3.6 cm 2 and a length of 5 cm were used. As a harmful gas, propylene glycol methyl ether acetate (PGMEA) was used. The PGMEA at a flow rate of 6 L/min and air at a flow rate of 4 L/min were mixed and injected. The PGMEA was injected at an injection amount of 135.02 ppm, and after a catalytic reaction, the amount was 0.71 ppm, showing a decomposition efficiency of 99.47%. In addition, total volatile organic compounds (TVOC) were injected at an injection amount of 136.64 ppm, and after a catalytic reaction, the amount was 0.83 ppm, showing a decomposition efficiency of 99.39%.

Harmful Substance Removing Apparatus

Hereinafter, a harmful substance removing apparatus according to an embodiment of the present invention will be described in detail.

Figure 10:
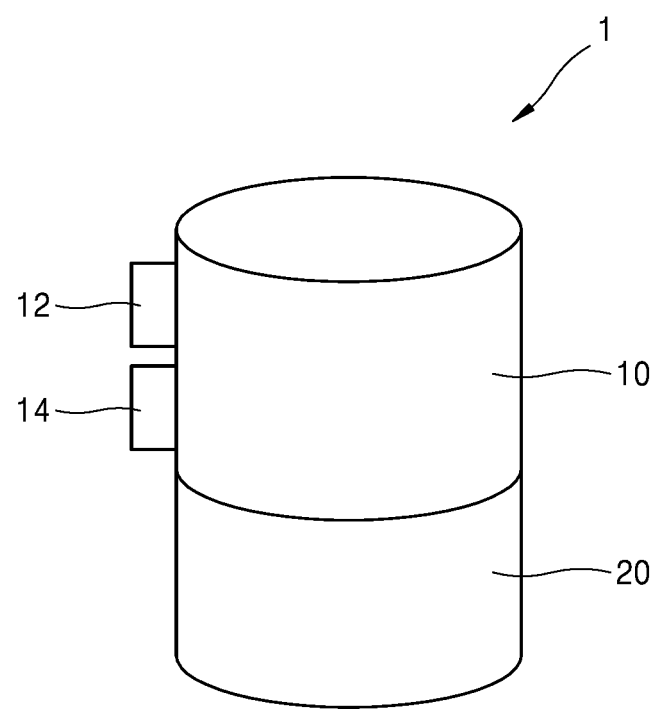
FIG. 10 is a schematic diagram illustrating a harmful substance removing apparatus according to an embodiment of the present invention.

FIG. 10 is a schematic diagram illustrating a harmful substance removing apparatus according to an embodiment of the present invention.

Referring to FIG. 10, the harmful substance removing apparatus 1 includes a harmful substance removal module 10; and a catalyst module 20 for removing residual ozone that removes residual ozone generated in the harmful substance removal module 10.

According to the technical idea of the present invention, the harmful substance removal module 10 includes a plasma generator to generate plasma and functions to remove harmful substances. The harmful substance removal module 10 may include a plasma generator 12 configured to generate low-temperature plasma or room-temperature plasma to remove harmful substances, and may generate active species, such as ozone, with high efficiency under high-speed wind and low pressure loss conditions. In addition, the harmful substance removal module 10 may convert the active species and employ a surface material technology for surface oxidation in order to increase the harmful substance removal performance.

In addition, the harmful substance removal module 10 may include an ultraviolet ray generator 14 for removing harmful substances. The ultraviolet ray generator generates ultraviolet rays to remove harmful substances.

In FIG. 10, the plasma generator 12 and the ultraviolet ray generator 14 are shown as being disposed outside the harmful substance removal module 10, but this is exemplary and the plasma generator 12 and the ultraviolet ray generator 14 may be disposed in various ways. For example, only one of the plasma generator 12 and the ultraviolet ray generator 14 may be disposed, the disposition order of the plasma generator 12 and the ultraviolet ray generator 14 may be reverse to each other, or the plasma generator 12 and the ultraviolet ray generator 14 may be disposed inside the harmful substance removal module 10.

In addition, the harmful substance removal module 10 may further include a ceramic material for removing harmful substances. The ceramic material may include a ceramic nanofiber filter, and a conductive ceramic heating carrier technology for a low-temperature catalyst may be applied.

The harmful substances may include a harmful gas to be removed. Examples of the harmful substances may include at least one of, for example, volatile organic compounds (VOCs), nitrogen oxides (NOx) that are exhausted from vehicles or boilers and cause greenhouse effects and acid rain, various odors, various hydrocarbons (CxHy), carbon monoxide (CO), harmful radicals, pathogens, or viruses. However, these are exemplary and the technical idea of the present invention is not limited thereto.

The catalyst module 20 for removing residual ozone functions to decompose residual ozone generated in the harmful substance removal module 10. The catalyst module 20 for removing residual ozone may incorporate a low-temperature activation technology for decomposing residual ozone, a catalyst reaction control technology using a heating carrier, and a residual ozone-radical-catalyst reaction analysis technology. In addition, the catalyst module 20 for removing residual ozone may function to further decompose harmful substances such as volatile organic compounds in addition to pathogens.

Although in the harmful substance removing apparatus 1 of FIG. 10, the harmful substance removal module 10 and the catalyst module 20 for removing residual ozone are illustrated in a cylindrical shape with the same diameter, this is exemplary and the technical idea of the present invention is not limited to this shape. In addition, although the harmful substance removal module 10 and the residual ozone removal catalyst module 20 are shown as being in contact with each other, the case where they are spaced apart from each other is also included in the technical idea of the present invention. In other words, the harmful substance removing apparatus 1 according to the technical idea of the present invention may include various structures and arrangements that can achieve the function of removing residual ozone generated by the harmful substance removal module 10 from the catalyst module 20 for removing residual ozone.

In the harmful substance removing apparatus 1, the harmful substance removal module 10 may remove harmful substances by active species such as ozone generated through plasma, and the catalyst module 20 for removing residual ozone may remove residual ozone remaining after removing the harmful substances so that the residual ozone is not released to the outside. The harmful substance removal module 10 and the catalyst module 20 for removing residual ozone may have the same contact cross-sectional areas so that the residual ozone is not discharged to the outside. Also, a contact area between the harmful substance removal module 10 and the catalyst module 20 for removing residual ozone may be sealed.

The harmful substance removing apparatus 1 may preferably control residual ozone to 0.1 ppm or less, more preferably 0.05 ppm or less. In addition, for application to air conditioning of multi-use facilities, the harmful substance removing apparatus 1 uses a compact low backpressure monolithic catalyst that can be applied in a limited space under high flow and high wind speed conditions. In order to realize such a compact catalyst, a heating carrier is used, and coating technology and catalytic reaction control technology for application to a large area heating carrier are applied.

Also, the harmful substance removing apparatus 1 according to the technical idea of the present invention may be applied to removal of harmful gases. Technologies for effectively removing harmful gases that greatly change the atmospheric environment have been actively studied in recent years. These harmful gases include various substances and organisms that are used in chemical processes and are fatally toxic to the human body. For example, among the harmful gases, volatile organic compounds contain many first-class carcinogens designated by the World Health Organization (WHO). Exposure for a long time to such harmful gases may cause reduced immunity thereby contributing to development of a variety of serious diseases including respiratory diseases such as colds, asthma, bronchitis, etc., cardiovascular diseases, skin diseases, eye diseases, and the like. In addition, as the representative precursor substances of fine particles, the harmful gases may form secondary fine particles in the atmospheric air when they are discharged, threating the human health and deteriorating the air quality. Technologies for removing harmful gases through chemical decomposition use catalysts to accelerate the decomposition reaction. In a reaction using a catalyst, the catalyst is heated to a normal operating temperature range and used in order to maximize the catalyst efficiency. In general, a heating source is disposed outside the catalyst module, and when external heating is used, energy loss is large, and hence the external heating is not suitable for fields requiring low energy. In addition, most of the existing harmful gas reduction technologies are implemented through centralized large-scale reduction facilities, and such large-scale reduction facilities are generally installed in industrial sites where harmful gases are generated in relatively high concentrations, making it difficult to apply the existing technologies directly to the actual living environment of people. Furthermore, pellet or powder-type catalysts are used in large-scale harmful substance removing apparatuses through a simple structure, but development of technologies for miniaturized/commoditized indoor reduction apparatuses is urgently needed in that high costs and periodic replacement are required due to the use of large amount of catalysts.

Figure 11:
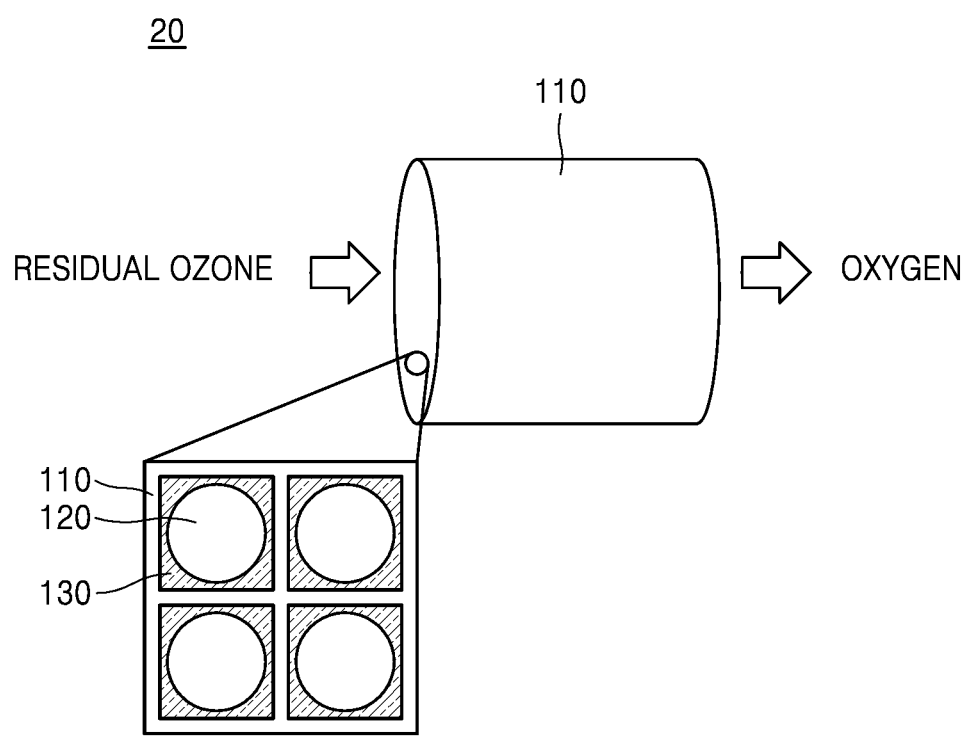
FIG. 11 is a schematic diagram illustrating a catalyst module for removing residual ozone of a harmful substance removing apparatus according to an embodiment of the present invention.

FIG. 11 is a schematic diagram illustrating a catalyst module 20 for removing residual ozone of a harmful substance removing apparatus according to an embodiment of the present invention.

Referring to FIG. 11, the catalyst module 20 for removing residual ozone includes a heating carrier 110 and a catalyst region 130. The heating carrier 110 may be composed of an electrically heatable heating body, may include one or more flow channels 120 therein, through which a fluid can flow, and may have a porous structure having a plurality of pores. The heating carrier 110 may include a plurality of flow channels 120 extending from one end to the opposite end thereof. Since the components of the catalyst module for removing harmful gas described above with reference to FIG. 1 are applicable to the catalyst module 20 for removing residual ozone, redundant descriptions of the components will be omitted.

The fluid may include residual ozone to be removed. Also, the fluid may include harmful gases. However, these are exemplary and the technical idea of the present invention is not limited thereto.

A manufacturing method of a harmful substance removing apparatus according to an embodiment of the present invention may be a manufacturing method of a harmful substance removing apparatus including a harmful substance removal module and a catalyst module for removing residual ozone that removes residual ozone generated in the harmful substance removal module. In the manufacturing method of a harmful substance removing apparatus, a manufacturing method of the catalyst module for removing residual ozone may include providing a heating carrier that is composed of an electrically heatable heating body, includes one or more flow channels therein, and has a porous structure with pores; forming a first catalyst layer having a first catalyst material loading amount in the pores of the heating carrier; and forming a second catalyst layer applied on an inner surface of the heating carrier and having a second catalyst material loading amount higher than the first catalyst material loading amount.

Since the manufacturing method of the catalyst module for removing harmful gas described above with reference to FIGS. 2 to 5 is applicable to the manufacturing method of the catalyst module for removing residual ozone, redundant description will be omitted.

In addition, a manufacturing method of a harmful substance removing apparatus includes: providing a heating carrier that is composed of an electrically heatable heating body, includes one or more flow channels therein, and has a porous structure with pores; filling at least a portion of the pores formed on an inner surface of the flow channel with a fluid; coating the inner surface of the flow channel with a catalyst solution by introducing the catalyst solution placed outside the flow channel into the flow channel by means of a pressure difference; and forming a catalyst layer on the inner surface of the flow channel by drying the coated catalyst solution.

Since the manufacturing method of the catalyst module for removing harmful substance described above with reference to FIG. 6 is applicable to the manufacturing method of the catalyst module for removing residual ozone, redundant description will be omitted.

Since the apparatus for manufacturing a catalyst module for removing harmful gas described above with reference to FIG. 7 is applicable to an apparatus for manufacturing a catalyst module for removing residual ozone that performs the manufacturing method of a catalyst module for removing residual ozone of the harmful substance removing apparatus and a method of coating a heating carrier with a catalyst material, redundant description will be omitted.

Since the catalyst system for removing harmful gas and the operating method thereof described above with reference to FIGS. 8 and 9 are applicable to a harmful substance removing system configured using the harmful substance removing apparatus and an operating method thereof, redundant description will be omitted. Here, the catalyst module 410 for removing harmful gas may be used as a catalyst module for removing residual ozone.

A method of removing residual ozone using the harmful substance removing system will be described.

When power is supplied to the heating carrier, the heating carrier may be self-heated. The temperature of the heating carrier may be rapidly raised and maintained within an operating range in which a catalyst can efficiently operate by a predetermined power supply value.

In the harmful substance removing system, the heating of the heating carrier is realized by self-heating of the heating carrier, which is an electrical resistance heating body, rather than by an external heat source. That is, electric power is directly applied to the heating carrier to heat the heating carrier. Therefore, as compared to the conventional heating by heat energy input from an external source, a response to temperature change according to power input is remarkably fast. Accordingly, it is possible to rapidly heat the heating carrier by controlling the waveform of the power input to the heating carrier. For example, when power in the form of a pulse is supplied to the heating carrier for a short time through the power supply unit, the heating carrier also exhibits a temperature change in the form of a pulse.

Meanwhile, the heating carrier may be rapidly heated when power in the form of a pulse is applied, and may also be rapidly cooled at a room temperature or in a cold air when the applied power is removed. For example, the catalyst module is cooled back to the temperature before it was heated and then waits until it is heated.

Residual ozone is introduced into the flow channel of the heated heating carrier and then flows along the flow channel of the heating carrier. During this process, the residual ozone may be decomposed while the decomposition reaction is accelerated by the catalyst region. This process corresponds to "reaction stage" shown in FIG. 9. The residual ozone is decomposed into an oxygen gas ($O_2$) and the like in the catalyst region, and is discharged to the outside through the flow channel at the opposite end of the heating carrier.

Figure 12:
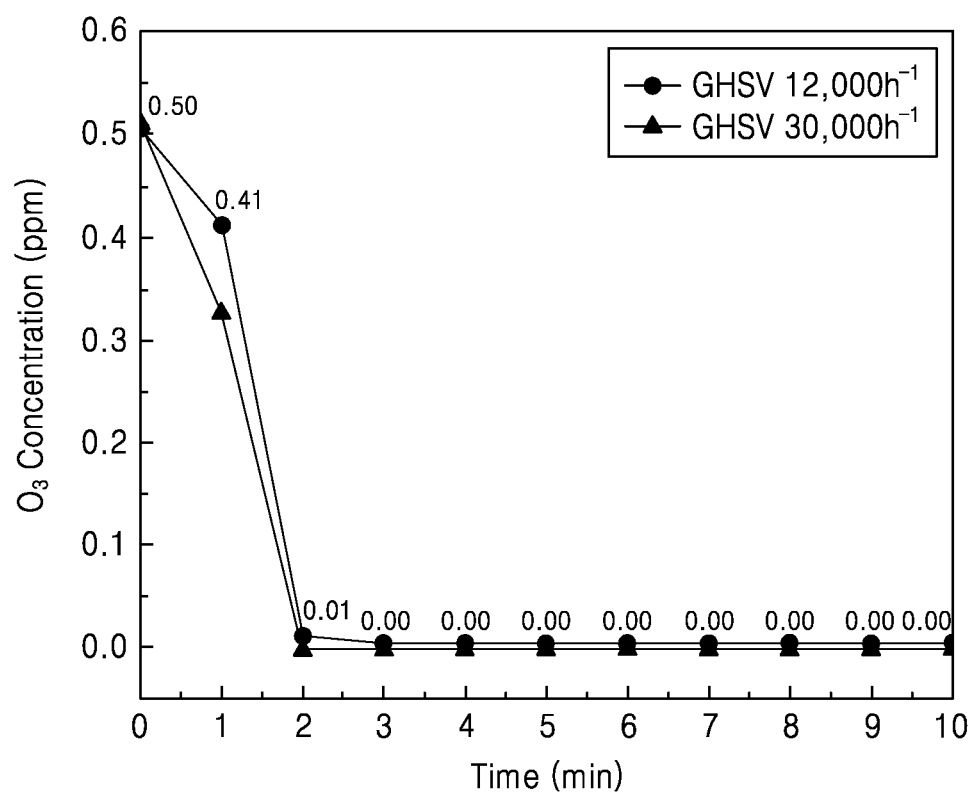
FIG. 12 is a graph showing ozone concentration over time as a result of removing residual ozone using a harmful substance removing apparatus according to an embodiment of the present invention.

FIG. 12 is a graph showing ozone concentration over time as a result of removing residual ozone using a harmful substance removing apparatus according to an embodiment of the present invention.

Referring to FIG. 12, it can be seen that the ozone concentration is initially about 0.5 ppm, but is reduced to 0.01 ppm or less after about 2 minutes. Such a delay in the reduction is due to the structure of a reactor and an analyzer, and in practice the ozone concentration is almost immediately reduced.

For reference, the manufacturing conditions and experimental conditions of FIG. 12 are as follows. SiC was used as a heating carrier, $Pd/Al_2O_3$ was used as a catalyst, the total loading amount of a catalyst material was 70 g/L, and the volume of the heating carrier was 53.76 $cm^3$. A temperature of an exhaust gas was 70° C. to 75° C., the space velocities (GHSV) were 12,000/h and 30,000/h, and the initial residual ozone concentration was 0.5 ppm.

While the present invention has been particularly shown and described with reference to embodiments thereof, it will be understood by one of ordinary skill in the art that various changes in form and details may be made therein without departing from the scope of the present invention as defined by the following claims.

INDUSTRIAL APPLICABILITY

According to an embodiment of the present invention, the catalyst module for removing harmful gas may have high efficiency of heat energy use and excellent heat exchange efficiency between catalyst and gas, and the catalyst module may be compactly arranged or integrated to enable miniaturization/commoditization of a harmful gas removing system at low cost.

According to an embodiment of the present invention, the harmful substance removing apparatus may implement plasma-catalyst or UV-catalyst integration to enable removal of harmful substances such as pathogens in indoor air, may provide the source technology of a unique catalyst manufacturing method and mass production technology, may realize price competitiveness of a catalyst module and miniaturization of a system that are essential for commercialization, and may allow commercialization of a catalytic reactor using a low-cost, high-efficiency nano-catalyst. The harmful substance removing apparatus can be applied to general hospitals, nursing hospitals, schools, kindergartens, subways, dense shopping malls, high-rise buildings, industrial sites, etc. to thereby reduce respiratory disease infections and reducing indoor harmful gases.

The invention claimed is:

1. A catalyst module for removing harmful gas, comprising:
a heating carrier comprising an electrically heatable heating body, the heating carrier including one or more flow channels inside, and having a porous structure with pores; and
a catalyst region formed on at least a portion of the surface of the heating carrier including the flow channels and containing a catalyst material for promoting a decomposition reaction of harmful gas passing through the flow channels,
wherein the heating carrier includes a plurality of flow channels extending from one end to an opposite end thereof,
wherein the one end of the flow channel is an inlet through which a fluid is introduced and the opposite end is an outlet through which the fluid is discharged,
wherein the heating carrier has the resistance in the range of $0.5\Omega$ to $500\Omega$, has a porosity in a range of 20% by volume to 70% by volume, and comprises SiC-based compound,
wherein the catalyst region comprises:
a first catalyst layer having a first catalyst material loading amount, the first catalyst layer formed in the pores of the heating carrier; and
a second catalyst layer applied on an inner surface of the first catalyst layer formed in the pores of the heating carrier, second catalyst layer having a second catalyst material loading amount higher than the first catalyst material loading amount.

2. The catalyst module of claim 1, wherein the first catalyst material loading amount is in the range of greater than 0 g/L to 50 g/L.

3. The catalyst module of claim 1, wherein the second catalyst material loading amount is in the range of 10 g/L to 220 g/L.

4. The catalyst module of claim 1, wherein the first catalyst layer is applied on the inner surface of the heating carrier.

5. The catalyst module of claim 1, further comprising an electrode connected to a portion of the heating carrier.

6. The catalyst module of claim 1, wherein the first and second catalyst materials include a metal including at least one of Pt, Pd, Rh, Ru, Fe, Cu, Ni, Mn, Co, Ag, Au, V, Ti, or Mo, a compound containing one or more of the above metals, or an oxide containing one or more of the above metals.

7. The catalyst module of claim 1, wherein the first and second catalyst materials include at least one of $MnO_2$, $Mn_2O_3$, MnO, $Mn_3O_4$, $CeO_2$, $TiO_2$, CuO, $V_2O_5$, ZnO, $SnO_2$, $SiO_2$, zeolite, or $Al_2O_3$.

8. The catalyst module of claim 7, wherein the first and second catalyst materials further include a doped element.

9. The catalyst module of claim 1, wherein the catalyst region further comprises a cocatalyst for accelerating catalytic activity and a binder for providing adhesion to the heating carrier.

10. A catalyst system for removing harmful gas, comprising:
the catalyst module for removing harmful gas of claim 1;
a power supply source configured to supply power to the catalyst module for removing harmful gas; and
a power control unit configured to control a waveform of the power input from the power supply source to the catalyst module for removing harmful gas.

11. The catalyst system of claim 10, wherein the power control unit further comprises a temperature control module configured to receive a temperature of the catalyst module for removing harmful gas and control a power value or waveform of the power to be input to the catalyst module for removing harmful gas according to the received temperature.

12. A manufacturing method of a catalyst module for removing harmful gas of claim 1, comprising:
providing a heating carrier composed of an electrically heatable heating body, including one or more flow channels therein, and having a porous structure with pores;
forming a first catalyst layer filled in at least part of the pores of the heating carrier and having a first catalyst material loading amount; and
forming a second catalyst layer applied on an inner surface of the heating carrier and having a second catalyst material loading amount higher than the first catalyst material loading amount,
wherein the heating carrier includes a plurality of flow channels extending from one end to an opposite end thereof,
wherein the one end of the flow channel is an inlet through which a fluid is introduced and the opposite end is an outlet through which the fluid is discharged,
wherein the heating carrier has a resistance in the range of $0.5\Omega$ to $500\Omega$, has a porosity in the range of 20% by volume to 70% by volume, and comprises SiC-based compound,
wherein the forming of the first catalyst layer is performed by immersing the heating carrier in a first catalyst solution having the first catalyst material loading amount,
wherein the forming of the second catalyst layer comprises coating an inner surface of the flow channel with a second catalyst solution by introducing the second catalyst solution having the second catalyst material loading amount and placed outside the flow passage into the flow channel using a pressure difference between the one end and the opposite end of the flow channel; and forming the second catalyst layer on the inner surface of the flow channel by drying the coated second catalyst solution.

13. A manufacturing method of a catalyst module for removing harmful gas of claim 1, comprising:

providing a heating carrier composed of an electrically heatable heating body, including one or more flow channels therein, and having a porous structure with pores;

filling at least a portion of the pores formed on an inner surface of the flow channel with a fluid;

coating the inner surface of the flow channel with a catalyst solution by introducing the catalyst solution placed outside the flow channel into the flow channel by means of a pressure difference between one end and an opposite end of the flow channel; and forming a catalyst layer on the inner surface of the flow channel by drying coated catalyst solution, wherein the heating carrier includes a plurality of flow channels extending from the one end to the opposite end thereof, wherein the one end of the flow channel is an inlet through which a fluid is introduced and the opposite end is an outlet through which the fluid is discharged, wherein the heating carrier has a resistance in the range of $0.5\Omega$ to $500\Omega$, has a porosity in the range of 20% by volume to 70% by volume, and comprises SiC-based compound.

* * * * *